(12) United States Patent
Kennedy

(10) Patent No.: US 6,264,603 B1
(45) Date of Patent: Jul. 24, 2001

(54) MIDDLE EAR VIBRATION SENSOR USING MULTIPLE TRANSDUCERS

(75) Inventor: Joel A. Kennedy, Arden Hills, MN (US)

(73) Assignee: St. Croix Medical, Inc., Minneapolis, MN (US)

(*) Notice: Subject to any disclaimer, the term of this patent is extended or adjusted under 35 U.S.C. 154(b) by 0 days.

(21) Appl. No.: 08/908,236

(22) Filed: Aug. 7, 1997

(51) Int. Cl.[7] .................................................. H04R 25/00
(52) U.S. Cl. .............................................. 600/25; 607/55
(58) Field of Search ............................... 600/25; 607/55, 607/56; 381/23.1, 312–331; 181/135

(56) References Cited

U.S. PATENT DOCUMENTS

| | | |
|---|---|---|
| 3,557,775 | 1/1971 | Mahoney . |
| 3,594,514 | 7/1971 | Wingrove . |
| 3,712,962 | 1/1973 | Epley . |
| 3,764,748 | 10/1973 | Branch et al. . |
| 3,931,648 | 1/1976 | Shea, Jr. . |
| 3,970,862 | 7/1976 | Edelman et al. . |
| 4,063,048 | 12/1977 | Kissiah, Jr. . |
| 4,063,049 | 12/1977 | Pipitone et al. . |
| 4,204,135 | 5/1980 | Murayamo . |
| 4,330,730 | 5/1982 | Kurz et al. . |
| 4,729,366 | 3/1988 | Schaefer . |
| 4,774,933 | 10/1988 | Hough et al. . |
| 4,776,322 | 10/1988 | Hough et al. . |
| 4,800,884 | 1/1989 | Heide et al. . |
| 4,817,607 | 4/1989 | Tatge . |
| 4,840,178 | 6/1989 | Heide et al. . |
| 4,850,962 | 7/1989 | Schaefer . |
| 4,957,478 | 9/1990 | Maniglia . |
| 4,988,333 | 1/1991 | Engebretson et al. . |
| 5,012,520 | 4/1991 | Steeger . |
| 5,015,224 | 5/1991 | Maniglia . |
| 5,015,225 | 5/1991 | Hough et al. . |
| 5,084,699 | 1/1992 | DeMichele . |
| 5,163,957 | 11/1992 | Sadé et al. . |
| 5,257,623 | 11/1993 | Karasev et al. . |
| 5,277,694 | 1/1994 | Leysieffer et al. . |
| 5,282,858 | 2/1994 | Bisch et al. . |
| 5,338,287 | 8/1994 | Miller et al. . |
| 5,360,388 | 11/1994 | Spindel et al. . |
| 5,411,467 | 5/1995 | Hortmann et al. . |
| 5,456,654 | 10/1995 | Ball . |
| 5,498,226 | 3/1996 | Lenkauskas . |
| 5,531,787 | 7/1996 | Lesinski et al. . |
| 5,554,096 | 9/1996 | Ball . |
| 5,558,618 | 9/1996 | Maniglia . |
| 5,624,376 | 4/1997 | Ball et al. . |
| 5,730,699 | * 3/1998 | Adams et al. ........................ 600/25 |
| 5,842,967 | * 12/1998 | Kroll ..................................... 600/25 |

OTHER PUBLICATIONS

Berlincourt, D., "Piezoelectric Ceramics: Characteristics and Applications," Journal of the Acoustical Society of America, 70,6:1586–1595, (1981).

(List continued on next page.)

Primary Examiner—Linda C. M. Dvorak
Assistant Examiner—R. Kearney
(74) Attorney, Agent, or Firm—Fredrikson & Byron, P.A.

(57) ABSTRACT

A hearing assistance system includes multiple middle ear transducers for sensing vibrations of an ossicle or other auditory element. The hearing assistance system is configured to accommodate an unknown or variable direction of the vibration. Two transducers are arranged to transduce nonidentical directional components of the vibration into electrical signals which are then combined. The combined electrical signal is approximately independent of the direction of the vibration, or has improved frequency response, or has an amplitude that is approximately independent of the direction of the vibration. The combined electrical signal may result from a square root of sum-of-squares, sum of individually filtered signals, differentiation, or other techniques. The hearing assistance system analogously accommodates three dimensional variability of the direction of vibration using three middle ear transducers.

4 Claims, 9 Drawing Sheets

OTHER PUBLICATIONS

Fredrickson, M.D., J.M., et al., "Ongoing Investigations into an Implantable Electromagnetic Hearing Aid for Moderate to Severe Sensorineural Hearing Loss," Otolaryngologic Clinics of North America, 28:107–120, (1995).

Goode, M.D., R.L., et al., "New Knowledge About the Function of the Human Middle Ear: Development of an Improved Analog Model," American Journal of Otology, 15:145–154, (1994).

Goode, M.D., R.L., et al., "Measurement of Umbo Vibration in Human Subjects–Method and Possible Clinical Applications," American Journal of Otology, 14:247–251, (1993).

Guinan, Jr., J.J., et al., "Middle–Ear Characteristics of Anesthetized Cats," Journal of the Acoustical Society of America, 41:1237–1261, (1967).

Gyo, K., et al., "Stapes Vibration Produced by the Output Transducer of an Implantable Hearing Aid," Archives of Otolaryngology Head and Neck Surgery, 113:1078–1081, (1987).

Gyo, K., et al., "Sound Pickup Utilizing an Implantable Piezoelectric Ceramic Bimorph Element: Application to the Cochlear Implant," American Journal of Otology, 5:273–276, (1984).

Jako, M.D., G.J., "Biomedical Engineering in Ear Surgery," Otolaryngologic Clinics of North America, 5:173–182, (1972).

Ko, PhD., W., "Engineering Principles of Mechanical Stimulation of the Middle Ear," Otolaryngologic Clinics of North America, 28:29–41, (1995).

Kodera, M.D., K., et al., "Sound Evaluation of Partially Implantable Piezoelectric Middle Ear Implant: Comparative Study of Frequency Responses," Ear, Nose and Throat Journal, 73:108–111, (1994).

Maniglia, M.D., A.J., et al., "Electromagnetic Implantabel Middle Ear Hearing Device of the Ossicular–Stimulating Type: Principles, Designs, and Experiments," Ann. Otol. Rhinol Laryngol, 97 (Suppl 136), part 2, (1988).

Nielsen, M.S., T.E., "Hearing Aid Characteristics and Fitting Techniques for Improving Speech Intelligibility in Noise," British Journal of Audiology, 10:1–7, (1976).

Nishihara, M.D., S., et al., "Effect of Changes in Mass on Middle Ear Function," Otolaryngology Head and Neck Surgery, 109:899–910, (1993).

Onchi, Y., "Mechanism of the Middle Ear," Journal of the Acoustical Society of America, 33:794–805, (1961).

Shaw, E.A.G., "Transformation of Sound Pressure Level from the Free Field to the Eardrum in the Horizontal Plane," Journal of the Acoustical Society of America, 56(6):1848–1861, (1974).

Suzuki, J.I., et al., "Principle, Construction and Indication of the Middle Ear Implant," Advances in Audiology, 4:15–21, (1988).

Villchur, E., "Signal Processing to Improve Speech Intelligibility in Perceptive Deafness," Journal of the Acoustical Society of America, 53:1646–1657, (1973).

Vlaming, M.S.M.G., et al., "Studies on the Mechanics of the Normal Human Middle Ear," Clin. Otolaryngol. 11:353–363, (1986).

Yanagihara, M.D., N., et al., "Partially Implantable Hearing Aid Using Piezoelectric Ceramic Ossicular Vibrator," Otolaryngologic Clinics of North America, 28:85–98, (1995).

Yanagihara, M.D., N., et al., "Development of an Implantable Hearing Aid Using a Piezoelectric Vibrator of Bimorph Design: State of the Art," Otolaryngology Head and Neck Surgery, 92: 706–712, (1984).

Yanagihara, M.D., N., et al., "Perception of Sound Through Direct Oscillation of the Stapes Using a Piezoelectric Ceramic Bimorph," Ann. Otol. Rhinol. Laryngol, 92:223–227, (1983).

Nosal, M.D., M.S.E.E., P.D., Letters from Paul Nosal, Letter, 1984–1986, (1984).

Riggs, M.T., "Powered Incus Replacement Prosthesis (SBIR Grant Application)," Letter, (1983).

Nuttall, A.L., "Laser Doppler Velocimetry of Basilar Membrane Vibration," Hearing Research, 51:203–214, (1991).

Maniglia, M.D., A.J., "A Contactless Electromagnetic Implantable Middle Ear Device for Sensorineural Hearing Loss," Ear, Nose and Throat Journal, 73(2), (1994).

Merchant, S.N., et al., "Acoustic Input Impedance of the Stapes and Cochlea in Human Temporal Bones," Hearing Research, 97:30–45, (1996).

Goode, R.L., et al., "Laser Doppler Vibrometer (LDV)—A New Clinical Tool for the Otologist," American Journal of Otology, 17:813–822, (1996).

Huttenbrink, K.B., "The Mechanics of the Middle–Ear at Static Air Pressures: The Role of the Ossicular Joints, the Function of the Middle–Ear Muscles and the Behaviour of Stapedial Prostheses," HNO–Universitatsklinik Munster West Germany, 1–35, (1988).

Suzuki, J.I., et al., "Long–Term Clinical Results of the Partially Implantable Piezoelectric Middle Ear Implant," Ear, Nose and Throat Journal, 73(2):104–107, (Feb. 1994).

Tos, M., et al., "Implantation of Electromagnetic Ossicular Replacement Device," Ear, Nose and Throat Journal, 73(2):93–103, (Feb. 1994).

* cited by examiner

MIDDLE EAR VIBRATION SENSOR USING MULTIPLE TRANSDUCERS

CROSS REFERENCE TO RELATED APPLICATIONS

This application is related to commonly assigned patent application entitled ELECTROMAGNETIC INPUT TRANSDUCERS FROM MIDDLE EAR SENSING, Ser. No. 08/907,424, filed on even date with the present application, now U.S. Pat. No. 5,993,376, issued Nov. 30, 1999, and assigned to the assignee of the present application, and which is herein incorporated by reference. This application is also related to commonly assigned patent application entitled CAPACITIVE INPUT TRANSDUCERS FOR MIDDLE EAR SENSING, Ser. No. 08/907,384, filed on even date with the present application, now U.S. Pat. No. 5,954,628, issued Sep. 21, 1999, and assigned to the assignee of the present application, and which is herein incorporated by reference. This application is also related to commonly assigned patent application entitled IMPLANTABLE HEARING SYSTEM HAVING MULTIPLE TRANSDUCERS, Ser. No. 08/693,430, filed on Aug. 7, 1996, now U.S. Pat. No. 5,997,466, issued Dec. 7, 1999, which disclosure is herein incorporated by reference.

THE FIELD OF THE INVENTION

This invention relates generally to at least partially implantable hearing assistance systems, and more particularly to the sensing of sound vibrations in the middle ear.

BACKGROUND

Some types of partial middle ear implantable (P-MEI), total middle ear implantable (T-MEI), cochlear implant, or other hearing assistance systems utilize components disposed within the middle ear or inner ear regions. Such components may include an input transducer for receiving sound vibrations or an output stimulator for providing mechanical or electrical output stimuli corresponding to the received sound vibrations.

An example of such a device is disclosed in U.S. Pat. No. 4,729,366, issued to D. W. Schaefer on Mar. 8, 1988. In the '366 patent, a mechanical-to-electrical piezoelectric input transducer is associated with the malleus bone in the patient's middle ear. The malleus vibrates in response to sounds received at the patient's tympanic membrane (eardrum). The piezoelectric input transducer transduces mechanical energy of malleus vibrations into an electrical signal, which is amplified and further processed by an electronics unit. A resulting electrical signal is provided to an electrical-to-mechanical piezoelectric output transducer that generates a mechanical vibration coupled to an element of the ossicular chain or to the oval window or round window. In the '366 patent, the ossicular chain is interrupted by removal of the incus. Removal of the incus prevents the mechanical vibrations delivered by the piezoelectric output transducer from mechanically feeding back to the piezoelectric input transducer.

Hearing assistance systems that sense sounds through corresponding ossicular vibrations face numerous difficulties. For example, the direction of motion of malleus vibrations varies unpredictably between individuals, making such vibrations difficult to transduce into a corresponding electrical signal, since sensors that transduce such vibrations typically perform optimally if the motion of the vibrations is in a particular direction. For example, a cantilevered piezoelectric bimorph input transducer provides a maximum output electrical signal amplitude when the direction of motion of the vibrations is perpendicular its longitudinal direction. A further complication is that the direction of motion of the malleus vibrations may be frequency dependent. As a result, an input transducer that is optimally positioned to sense malleus vibrations at a particular frequency in the audio frequency range may be inadequately positioned to sense malleus vibrations at a different frequency in the audio frequency range. There is a need in the art to provide sensing of sound vibrations in the inner ear, in which any variability in direction of motion of ossicular or other auditory elements is accommodated.

SUMMARY

The present invention includes a sensor for use with an at least partially implantable hearing assistance system. The sensor transduces a mechanical vibration of an auditory element into an electrical signal. A first input transducer is proportioned for transducing a first directional component of the mechanical vibration into a first electrical signal. A second input transducer is proportioned for transducing a second directional component of the mechanical vibration into a second electrical signal. The first and second input transducers are arranged such that the first and second directional components of the mechanical vibration are nonidentical. In one embodiment, a third input transducer is proportioned for transducing a third directional component of the mechanical vibration into a third electrical signal, such that the first, second, and third directional components of the mechanical vibration are nonidentical and linearly independent. The sensor is used in or with a hearing assistance system having an electronics unit that receives the electrical signals from the transducers, and provides a resulting combined electrical signal in response thereto.

The hearing assistance system also provides a method of transducing a mechanical vibration of an auditory element into at least one electrical signal. A first input transducer is positioned to transduce a first directional component of the mechanical vibration into a first electrical signal. A second input transducer is positioned to transduce a second directional component of the mechanical vibration into a second electrical signal. The first and second directional components of the mechanical vibration are nonidentical.

In one embodiment, the first and second electrical signals are combined. A first method of combining the first and second electrical signals squares each signal to provide resulting squared signals, sums the resulting squared signals to provide a sum-of-squares signal, and performs a square root function upon the resulting sum-of-squares signal to provide a resulting combined electrical signal. A second method of combining the first and second electrical signals individually filters the first and second electrical signals to provide resulting filtered signals, and sums the filtered signals to provide a resulting combined electrical signal. A third method of combining the first and second electrical signals differentiates the second electrical signal to provide a second differentiated electrical signal, and sums the second differentiated electrical signal with the first electrical signal to provide a resulting combined electrical signal.

In one embodiment, a third input transducer is positioned to receive a third directional component of the mechanical vibration. In this embodiment, the first, second, and third directional components of the mechanical vibration are nonidentical and linearly independent. The first, second, and third electrical signals are combined, such as by the above-described techniques. In one embodiment, the hearing assistance system includes an external programmer for adjusting hearing assistance parameters in a hearing assistance device and for data transmission from the hearing assistance device to the programmer, such as for parameter verification or diagnostic purposes. For example, the external programmer selects between the above-described signal combination techniques, in one embodiment of the present invention.

Thus, the present invention provides an improved hearing assistance system for sensing sound vibrations in the middle ear. The hearing assistance system accommodates variability in the direction of motion of an ossicular or other auditory element. This is particularly advantageous for sensing mechanical vibrations of an auditory element where the exact direction of the mechanical vibrations may be unknown, variable, or difficult to determine.

BRIEF DESCRIPTION OF THE DRAWINGS

In the drawings, like numerals describe substantially similar components throughout the several views.

DETAILED DESCRIPTION

In the following detailed description, reference is made to the accompanying drawings which form a part hereof, and in which is shown by way of illustration specific embodiments in which the invention may be practiced. These embodiments are described in sufficient detail to enable those skilled in the art to practice the invention, and it is to be understood that the embodiments may be combined, or that other embodiments may be utilized and that structural, logical and electrical changes may be made without departing from the scope of the present invention. The following detailed description is, therefore, not to be taken in a limiting sense, and the scope of the present invention is defined by the appended claims and their equivalents. In the accompanying drawings, like numerals describe substantially similar components throughout the several views.

The present invention provides a hearing assistance system for sensing mechanical vibrations of an auditory element, where the exact direction of the mechanical vibrations is unknown, variable, or difficult to determine. The invention is capable of use as or with a middle ear implantable hearing system such as a partial middle ear implantable (P-MEI), total middle ear implantable (T-MEI), cochlear implant, or other hearing system. A P-MEI or T-MEI hearing system assists the human auditory system in converting acoustic energy contained within sound waves into electrochemical signals delivered to the brain and interpreted as sound.

Figure 1:
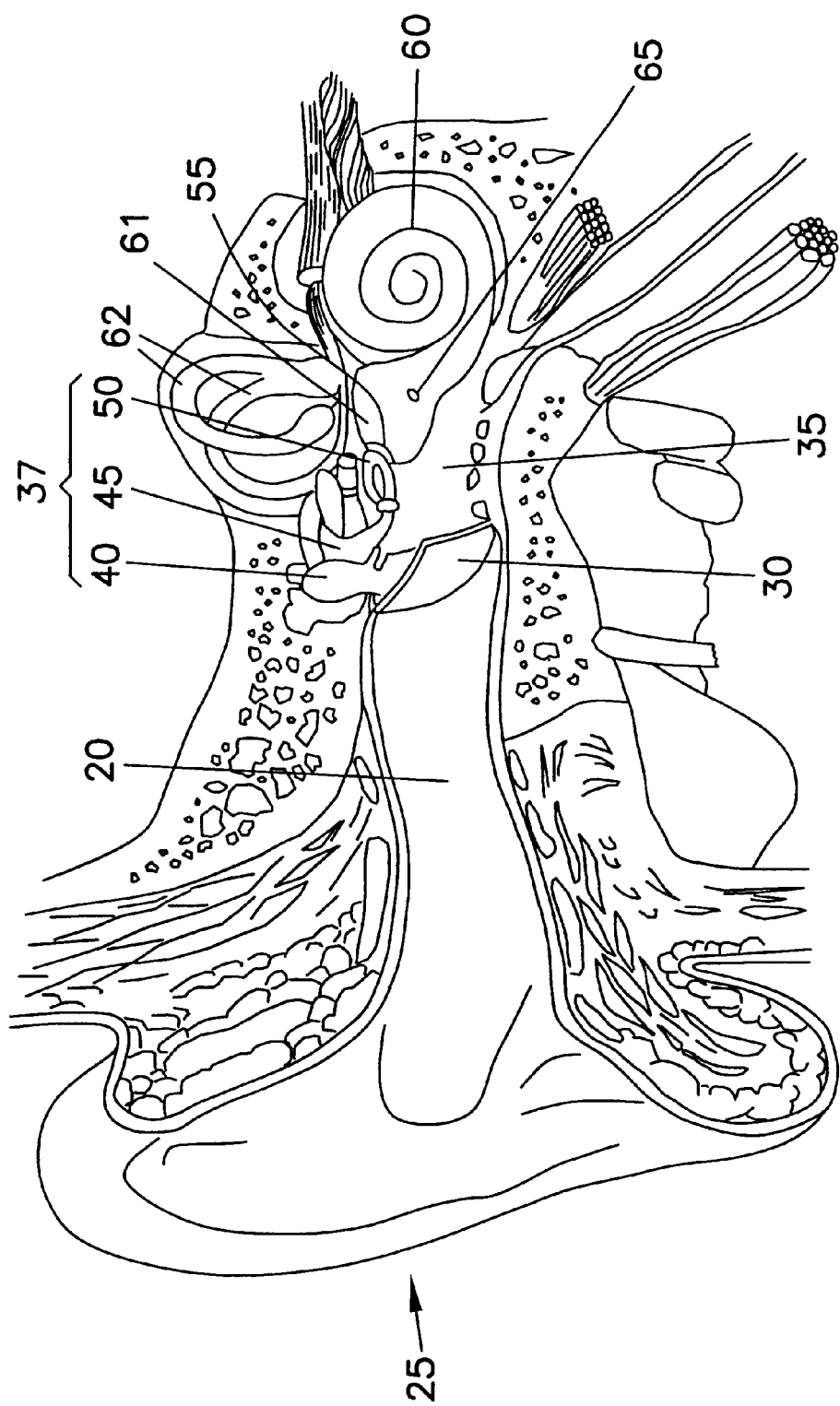
FIG. 1 illustrates generally a human auditory system.

FIG. 1 illustrates generally a human auditory system. Sound waves are directed into an external auditory canal 20 by an outer ear (pinna) 25. The frequency characteristics of the sound waves are slightly modified by the resonant characteristics of the external auditory canal 20. These sound waves impinge upon the tympanic membrane (eardrum) 30, interposed at the terminus of the external auditory canal 20, between it and the tynpanic cavity (middle ear) 35. Variations in the sound waves produce tympanic vibrations. The mechanical energy of the tympanic vibrations is communicated to the inner ear, comprising cochlea 60, vestibule 61, and semicircular canals 62, by a sequence of articulating bones located in the middle ear 35. This sequence of articulating bones is referred to generally as the ossicular chain 37. Thus, the tympanic membrane 30 and ossicular chain 37 transform acoustic energy in the external auditory canal 20 to mechanical energy at the cochlea 60.

The ossicular chain 37 includes three ossicles: a malleus 40, an incus 45, and a stapes 50. The malleus 40 includes manubrium and head portions. The manubrium of the malleus 40 attaches to the tympanic membrane 30. The head of the malleus 40 articulates with one end of the incus 45. The incus 45 normally couples mechanical energy from the vibrating malleus 40 to the stapes 50. The stapes 50 includes a capitulum portion, comprising a head and a neck, connected to a footplate portion by means of a support crus comprising two crura. The stapes 50 is disposed in and against a membrane-covered opening on the cochlea 60. This membrane-covered opening between the cochlea 60 and middle ear 35 is referred to as the oval window 55. Oval window 55 is considered part of cochlea 60 in this patent application. The incus 45 articulates the capitulum of the stapes 50 to complete the mechanical transmission path.

Normally, prior to implantation of the invention, tympanic vibrations are mechanically conducted through the malleus 40, incus 45, and stapes 50, to the oval window 55. Vibrations at the oval window 55 are conducted into the fluid-filled cochlea 60. These mechanical vibrations generate fluidic motion, thereby transmitting hydraulic energy within the cochlea 60. Pressures generated in the cochlea 60 by fluidic motion are accommodated by a second membrane-covered opening on the cochlea 60. This second membrane-covered opening between the cochlea 60 and middle ear 35 is referred to as the round window 65. Round window 65 is considered part of cochlea 60 in this patent application. Receptor cells in the cochlea 60 translate the fluidic motion into neural impulses which are transmitted to the brain and perceived as sound. However, various disorders of the tympanic membrane 30, ossicular chain 37, and/or cochlea 60 can disrupt or impair normal hearing.

Hearing loss due to damage in the cochlea 60 is referred to as sensorineural hearing loss. Hearing loss due to an inability to conduct mechanical vibrations through the middle ear 35 is referred to as conductive hearing loss. Some patients have an ossicular chain 37 lacking sufficient resiliency to transmit mechanical vibrations between the tympanic membrane 30 and the oval window 55. As a result, fluidic motion in the cochlea 60 is attenuated. Thus, receptor cells in the cochlea 60 do not receive adequate mechanical stimulation. Damaged elements of ossicular chain 37 may also interrupt transmission of mechanical vibrations between the tympanic membrane 30 and the oval window 55.

Various techniques have been developed to remedy hearing loss resulting from conductive or sensorineural hearing disorder. For example, tympanoplasty is used to surgically reconstruct the tympanic membrane 30 and establish ossicular continuity from the tympanic membrane 30 to the oval window 55. Various passive mechanical prostheses and implantation techniques have been developed in connection with reconstructive surgery of the middle ear 35 for patients with damaged elements of ossicular chain 37. Two basic forms of prosthesis are available: total ossicular replacement prostheses (TORP), which is connected between the tympanic membrane 30 and the oval window 55; and partial ossicular replacement prostheses (PORP), which is positioned between the tympanic membrane 30 and the stapes 50.

Various types of hearing aids have been developed to compensate for hearing disorders. A conventional "air conduction" hearing aid is sometimes used to overcome hearing loss due to sensorineural cochlear damage or mild conductive impediments to the ossicular chain 37. Conventional hearing aids utilize a microphone, which transduces sound into an electrical signal. Amplification circuitry amplifies the electrical signal. A speaker transduces the amplified electrical signal into acoustic energy transmitted to the tympanic membrane 30. However, some of the transmitted acoustic energy is typically detected by the microphone, resulting in a feedback signal which degrades sound quality. Conventional hearing aids also often suffer from a significant amount of signal distortion.

Implantable hearing systems have also been developed, utilizing various approaches to compensate for hearing disorders. For example, cochlear implant techniques implement an inner ear hearing system. Cochlear implants electrically stimulate auditory nerve fibers within the cochlea 60. A typical cochlear implant system includes an external microphone, an external signal processor, and an external transmitter, as well as an implanted receiver and an implanted single channel or multichannel probe. A single channel probe has one electrode. A multichannel probe has an array of several electrodes. In the more advanced multichannel cochlear implant, a signal processor converts speech signals transduced by the microphone into a series of sequential electrical pulses corresponding to different frequency bands within a speech frequency spectrum. Electrical pulses corresponding to low frequency sounds are delivered to electrodes that are more apical in the cochlea 60. Electrical pulses corresponding to high frequency sounds are delivered to electrodes that are more basal in the cochlea 60. The nerve fibers stimulated by the electrodes of the cochlear implant probe transmit neural impulses to the brain, where these neural impulses are interpreted as sound.

Other inner ear hearing systems have been developed to aid patients without an intact tympanic membrane 30, upon which "air conduction" hearing aids depend. For example, temporal bone conduction hearing systems produce mechanical vibrations that are coupled to the cochlea 60 via a temporal bone in the skull. In such temporal bone conduction hearing systems, a vibrating element can be implemented percutaneously or subcutaneously.

A particularly interesting class of hearing systems includes those which are configured for disposition principally within the middle ear 35 space. In middle ear implantable (MEI) hearing assistance systems, an electrical-to-mechanical output transducer couples mechanical vibrations to the ossicular chain 37, which is optionally interrupted to allow coupling of the mechanical vibrations thereto. Both electromagnetic and piezoelectric output transducers have been used to effect the mechanical vibrations upon the ossicular chain 37.

One example of a partial middle ear implantable (P-MEI) hearing system having an electromagnetic output transducer comprises: an external microphone transducing sound into electrical signals; external amplification and modulation circuitry; and an external radio frequency (RF) transmitter for transdermal RF communication of an electrical signal. An implanted receiver detects and rectifies the transmitted signal, driving an implanted coil in constant current mode. A resulting magnetic field from the implanted drive coil vibrates an implanted magnet that is permanently affixed only to the incus 45. Such electromagnetic output transducers have relatively high power consumption requiring larger batteries, which limits their usefulness in total middle ear implantable (T-MEI) hearing systems.

A piezoelectric output transducer is also capable of effecting mechanical vibrations to the ossicular chain 37. An example of such a device is disclosed in U.S. Pat. No. 4,729,366, issued to D. W. Schaefer on Mar. 8, 1988. In the '366 patent, a mechanical-to-electrical piezoelectric input transducer is associated with the malleus 40, transducing mechanical energy into an electrical signal, which is amplified and further processed by an electronics unit. A resulting electrical signal is provided to an electrical-to-mechanical piezoelectric output transducer that generates a mechanical vibration coupled to an element of the ossicular chain 37 or to the oval window 55 or round window 65. In the '366 patent, the ossicular chain 37 is interrupted by removal of the incus 45. Removal of the incus 45 prevents the mechanical vibrations delivered by the piezoelectric output transducer from mechanically feeding back to the piezoelectric input transducer.

Figure 2:
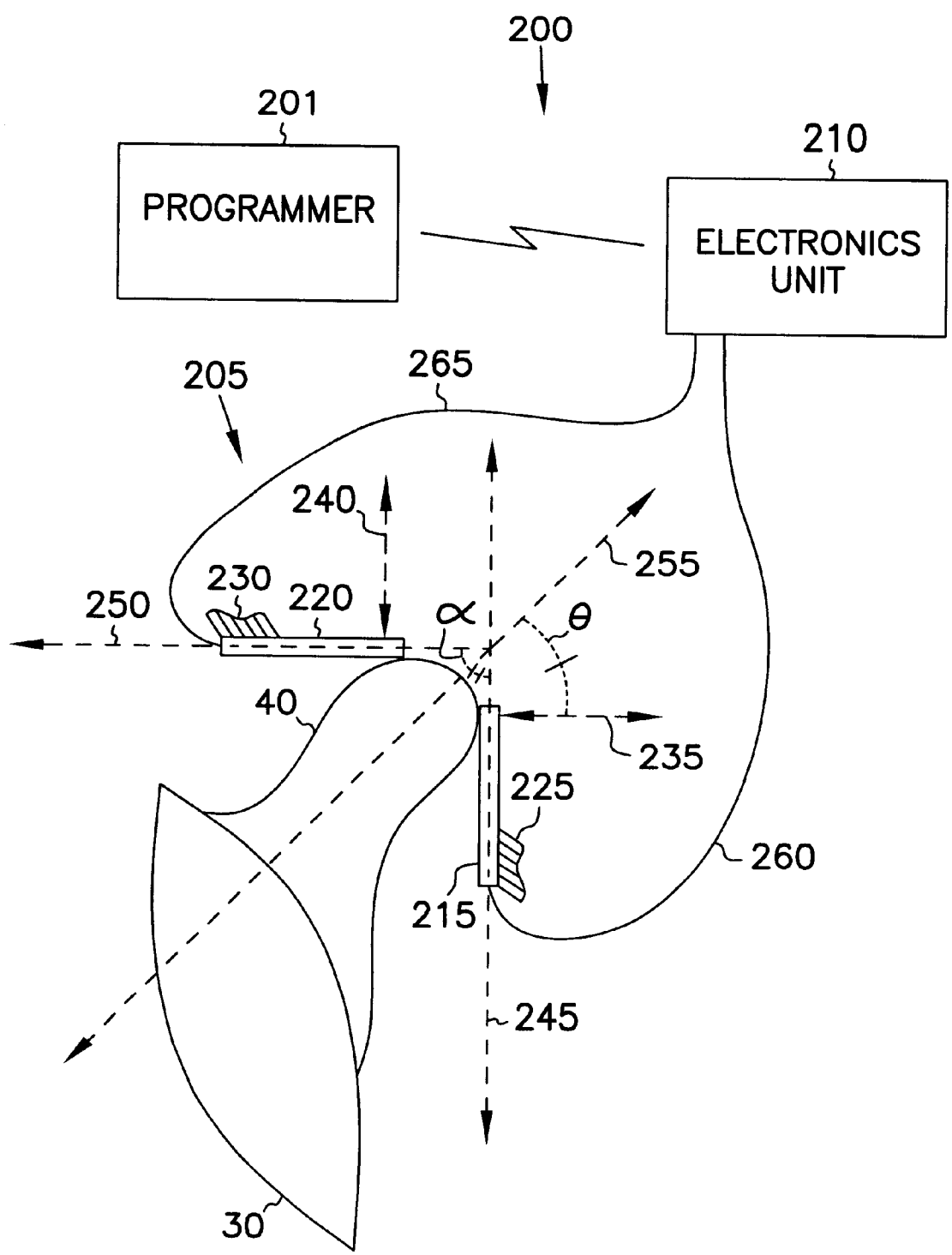
FIG. 2 is a schematic/block diagram illustrating generally one embodiment of a hearing assistance system according to the present invention.

FIG. 2 is a schematic/block diagram illustrating generally one embodiment of a hearing assistance system according to the present invention, including a hearing assistance device 200 for sensing mechanical vibrations of an auditory element, where the exact direction of the mechanical vibrations may be unknown, variable, or difficult to determine.

The hearing assistance system also includes an external (i.e., not implanted) programmer 201, which is communicatively coupled to an external or implantable portion of hearing assistance device 200. Programmer 201 includes hand-held, desktop, or a combination of hand-held and desktop embodiments, for use by a physician or the patient in which hearing assistance device 200 is implanted.

In one embodiment, each of programmer 201 and hearing assistance device 200 include an inductive element, such as a coil, for inductively-coupled bi-directional transdermal communication between programmer 201 and hearing assistance device 200. Inductive coupling is just one way to communicatively couple programmer 201 and hearing assistance device 200. Any other suitable technique of communicatively coupling programmer 201 and hearing assistance device 200 may also be used.

In one embodiment, such communication includes programming of hearing assistance device 200 by programmer 201 for adjusting hearing assistance parameters in hearing assistance device 200, and also provides data transmission from hearing assistance device 200 to programmer 201, such as for parameter verification or diagnostic purposes. Programmable parameters include, but are not limited to: on/off, standby mode, type of noise filtering for a particular sound environment, frequency response, volume, delivery of a test stimulus on command, and any other programmable parameter.

Hearing assistance device 200 includes a sensor 205 that is electrically coupled to an electronics unit 210. In the embodiment of FIG. 2, malleus 40 is illustrated, by way of example, as the auditory element from which vibrations are sensed, but other auditory elements could also be used, including, but not limited to tympanic membrane 30, incus 45 or other ossicle, or any prosthetic auditory element serving a similar function.

Sensor 205 includes more than one electromechanical transducer element. In the embodiment of FIG. 2, sensor 205 includes a first input transducer 215 and a second input transducer 220. In FIG. 2, first input transducer 215 and second input transducer 220 are each illustrated, by way of example, as piezoelectric ceramic bimorph transducers that are proportioned for disposition within the middle ear 35 region for receiving mechanical vibrations from malleus 40. However, other embodiments of the invention include other types of transducers. In one embodiment, at least one of first and second input transducers 215 and 220 includes a piezoelectric film such as a polarized fluoropolymer, e.g. polyvinylidene fluoride (PVDF). For this application, a PVDF film such as that sold under the trademark "Kynar" by AMP, Inc. of Harrisburg, Pa., is one example of a material that can be used for the piezoelectric film. In other embodiments, at least on of first and second input transducers 215 and 220 includes an accelerometer, electromagnetic input transducer, or capacitive input transducer. Example of electromagnetic input transducers are described in a co-pending patent application entitled ELECTROMAGNETIC INPUT TRANSDUCERS FOR MIDDLE EAR SENSING, Ser. No. 08/907,424, filed on even date with the present application, now U.S. Pat. No. 5,993,376, issued Nov. 30, 1999, and assigned to the assignee of the present application, and which is herein incorporated by reference. Examples of capacitive input transducers are described in co-pending patent application entitled CAPACITIVE INPUT TRANSDUCERS FOR MIDDLE EAR SENSING, Ser. No. 08/907,384, filed on even date with the present application, now U.S. Pat. No. 5,954,628, issued Sep. 21, 1999, and assigned to the assignee of the present application, and which is herein incorporated by reference.

These and other different types of input transducers may be used in combination for many purposes, including to optimize overall frequency response by using a different type of first input transducer 215 than second input transducer 220. For example, first input transducer 215 may be a piezoelectric ceramic bimorph type and second input transducer 220 may be an accelerometer type. First input transducer 215 and second input transducer 220 may also be of the same type, e.g. both piezoelectric ceramic bimorphs, but having different frequency response characteristics, e.g. by having different physical dimensions.

In FIG. 2, respective first and second input transducers 215 and 220 are typically cantilevered from respective first and second mounts 225 and 230, which are affixed, such as to the temporal bone peripheral to middle ear 35 region or elsewhere. The mechanical vibrations of malleus 40 cause vibratory displacements of the ends of respective first and second input transducers 215 and 220 that are distal to respective first and second mounts 225 and 230. As a result, the vibrations of malleus 40 are resolved into nonidentical respective first and second directional components 235 and 240 by first and second input transducers 215 and 220, as described in detail below.

First and second input transducers 215 and 220 are arranged in a predetermined spatial relationship. For example, respective first and second mounts 225 and 230 may be integrally formed as a unitary carrier of respective first and second transducers 215 and 220, or may be otherwise mechanically coupled to such a carrier. Any carrier that provides a predetermined spatial arrangement of first and second input transducers 215 and 220 may be used. In one embodiment, first and second transducers 215 and 220 are configured to provide a predetermined angular spacing of angle, α, between a first longitudinal direction 245 of first transducer 215 and a second longitudinal direction 250 of second transducer 220. As a result, a predetermined angle of magnitude (180-α) degrees is provided between respective first and second directional components 235 and 240. FIG. 2 illustrates one particular embodiment in which a is approximately equal to 90 degrees, i.e. first transducer 215 and second transducer 220 are approximately orthogonally disposed with respect to each other, though other arrangements are also possible, as explained below.

The hearing assistance device 200 accommodates vibratory displacements of malleus 40 even if such vibrations are in a malleus vibration direction 255 that is variable between patients, or is not exactly known for the particular patient, or is variable as a function of frequency or other parameter for the particular patient. The vibrations of malleus 40 are resolved into respective first and second directional components 235 and 240 by respective first and second input transducers 215 and 220, providing resulting voltage signals such as respective first and second electrical signals $v_{235}(t)$ and $v_{240}(t)$ that are coupled via respective first and second leads 260 and 265 to electronics unit 210. In one embodiment, respective first and second transducers 215 and 220 are disposed for an approximately orthogonal relationship between respective first and second directional components 235 and 240. Electronics unit 210 combines the first and second electrical signals $v_{235}(t)$ and $v_{240}(t)$, using one of a number of different techniques that are described below. In one embodiment, the combination of first and second electrical signals $v_{235}(t)$ and $v_{240}(t)$ provides a resulting signal having an amplitude that is substantially independent of the vibration direction 255, as described below.

An angle θ is formed between the vibration direction 255 and its first directional component 235. Equation (1) illustrates the displacement in vibration direction 255 resulting from vibrations of malleus 40.

$$d_{255}(t) = D_{255} \sin(\omega t) \qquad (1)$$

In Equation (1), $d_{255}(t)$ represents the displacement signal resulting from the vibrations of malleus 40, in the vibration direction 255, as a function of time; $D_{255}$ represents the amplitude of the displacement in the vibration direction 255; ω represents the angular frequency of the vibratory displacement; and t represents time. A displacement signal $d_{235}(t)$ of the first directional component 235 of the vibration of malleus 40 is illustrated by Equation (2).

$$d_{235}(t) = D_{255} \cos(\theta)\sin(\omega t) \qquad (2)$$

A displacement signal $d_{240}(t)$ of the second directional component 240 of the vibration of malleus 40 is illustrated by Equation (3).

$$d_{240}(t)=D_{255}\sin(\theta)\sin(\omega t) \quad (3)$$

First transducer 215 transduces the displacement signal $d_{235}(t)$ of the first directional component 235 of the vibration of malleus 40 into a corresponding first electrical signal $v_{235}(t)$ of amplitude $V_{255}\cos(\theta)$, illustrated by Equation (4), which is provided to electronics unit 210 through first lead 260.

$$v_{235}(t)=V_{255}\cos(\theta)\sin(\omega t) \quad (4)$$

Second transducer 220 transduces the displacement signal $d_{240}(t)$ of the second directional component 240 of the vibration of malleus 40 into a corresponding second electrical signal $v_{240}(t)$ of amplitude $V_{255}\sin(\theta)$, illustrated by Equation (5), which is provided to electronics unit 210 through second lead 265.

$$v_{240}(t)=V_{255}\sin(\theta)\sin(\omega t) \quad (5)$$

Figure 3:
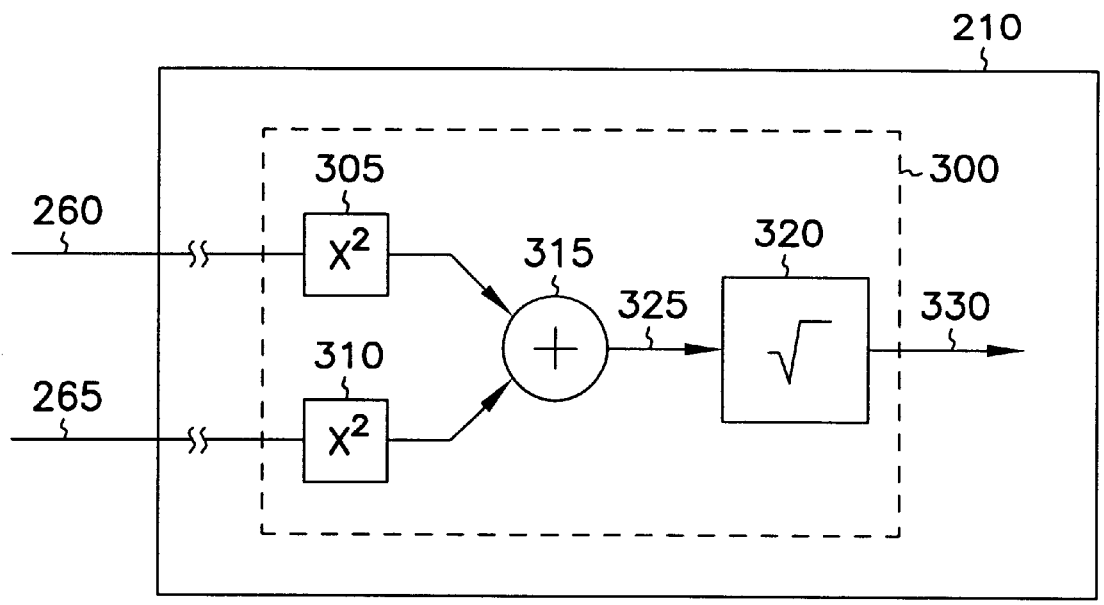
FIG. 3 is a block diagram illustrating one embodiment of a portion of the electronics unit of FIG. 2 in more detail.

FIG. 3 is a block diagram illustrating one embodiment of a portion of electronics unit 210 in more detail. In FIG. 3, electronics unit 210 includes a signal combiner 300 that receives first electrical signal $v_{235}(t)$ and second electrical signal $v_{240}(t)$, which are coupled thereto from respective first and second leads 260 and 265. However, signal preprocessing or other components may be interposed between signal combiner 300 and each of first and second leads 260 and 265, such as for prefiltering and analog-to-digital conversion. Signal combiner 300 includes a first squaring circuit 305, a second squaring circuit 310, a summer 315, and a square root circuit 320, each of which are implemented in hardware, in one embodiment, or as a sequence of instructions executable on a microprocessor, in an alternative embodiment.

First and second squaring circuits 305 and 310, respectively, receive and square, i.e. raise to the second power, respective first and second electrical signals $v_{235}(t)$ and $v_{240}(t)$, and provide resulting respective first and second squared electrical signals to summer 315. Summer 315 sums the first and second squared electrical signals, and provides at node 325 a resulting sum-of-squares electrical signal to square root circuit 320. Square root circuit 320 performs a square root function on the sum-of-squares electrical signal at node 325, and provides at node 330 a resulting combined electrical signal described by Equation (6).

$$v_{330}(t)=V_{255}\sin(\omega t) \quad (6)$$

In Equation (6), the resulting combined electrical signal at node 330, $v_{330}(t)$, is seen to be substantially independent of the angle $\theta$, upon which each of the first and second electrical signals $v_{235}(t)$ and $v_{240}(t)$ depended. As described above, since the angle $\theta$ may be either unknown or variable, the substantial independence of the combined electrical signal at node 330 from the angle $\theta$ provides a substantial advantage for hearing assistance signal processing.

Figure 4:
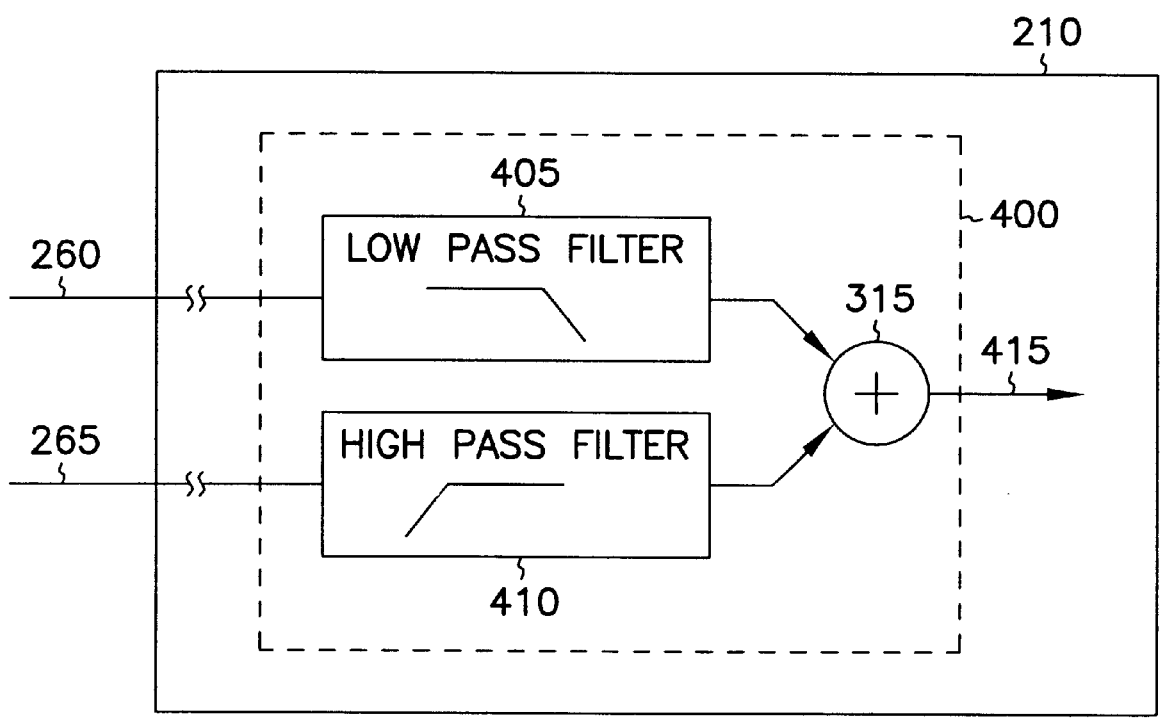
FIG. 4 is a block diagram illustrating another embodiment of a portion of electronics unit of FIG. 2 in more detail.

FIG. 4 is a block diagram illustrating another embodiment of a portion of electronics unit 210 in more detail. In FIG. 4, electronics unit 210 includes a signal combiner 400 that receives first electrical signal $v_{235}(t)$ and second electrical signal $v_{240}(t)$, which are coupled thereto from respective first and second leads 260 and 265. However, signal preprocessing or other components may be interposed between signal combiner 400 and each of first and second leads 260 and 265, such as for prefiltering and analog-to-digital conversion. Signal combiner 400 includes a first filter 405, a second filter 410, and the summer 315, each of which are implemented in hardware, in one embodiment, or as a sequence of instructions executable on a microprocessor, in an alternative embodiment.

In the embodiment of FIG. 4, first filter 405 is a low pass filter that receives the first electrical signal $v_{235}(t)$, and provides a resulting first filtered signal, which is low pass filtered, to summer 315. Second filter 410 is a high pass filter that receives the second electrical signal $v_{240}(t)$, and provides a resulting second filtered signal, which is high pass filtered, to summer 315. Summer 315 sums the electrical first and second filtered signals, and provides at node 415 a resulting combined electrical signal, $v_{415}(t)$, which comprises components of $v_{235}(t)$ for low frequencies, and which comprises components of $v_{240}(t)$ for high frequencies. In one embodiment, such as when the vibration direction 255 is frequency dependent, first transducer 215 and second transducer 220 are positioned to receive respective low frequency and high frequency orientations of vibration direction 255. As a result, signal combiner 400 advantageously improves frequency response by providing at node 415 a combined electrical signal, $v_{415}(t)$, of increased effective bandwidth.

In an alternative embodiment, low pass filter 405 and high pass filter 410 need not even be implemented as hardware or software incorporated within electronics unit 210. Instead, low pass filter 405 and high pass filter 410 are integrally implemented in respective first input transducer 215 and second input transducer 220, or vice-versa, having different frequency response characteristics, such as by using different types of transducers, or transducers of the same type having different physical dimensions, or other technique for obtaining different frequency response characteristics.

Figure 5:
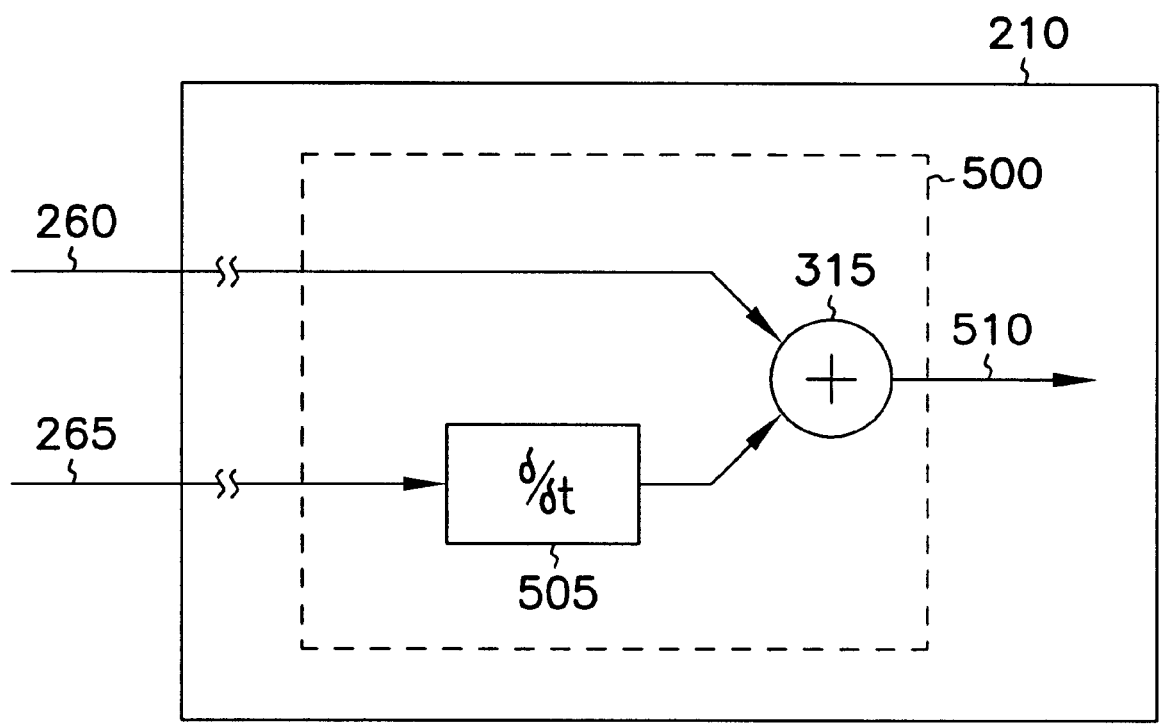
FIG. 5 is a block diagram illustrating another embodiment of a portion of electronics unit of FIG. 2 in more detail.

FIG. 5 is a block diagram illustrating another embodiment of a portion of electronics unit 210 in more detail. In FIG. 5, electronics unit 210 includes a signal combiner 500 that receives first electrical signal $v_{235}(t)$ and second electrical signal $v_{240}(t)$, which are coupled thereto from respective first and second leads 260 and 265. However, signal preprocessing or other components may be interposed between signal combiner 500 and each of first and second leads 260 and 265, such as for prefiltering and analog-to-digital conversion. Signal combiner 500 includes a differentiator 505, which is implemented in hardware, in one embodiment, or as a sequence of instructions executable on a microprocessor, in an alternative embodiment.

In the embodiment of FIG. 5, one of the first and second electrical signals $v_{235}(t)$ and $v_{240}(t)$, such as the first electrical signal $v_{235}(t)$, is coupled directly to summer 315. Differentiator 505 receives the other of the first and second electrical signals $v_{235}(t)$ and $v_{240}(t)$, such as second electrical signal $v_{240}(t)$, and provides a resulting second differentiated electrical signal, which is differentiated with respect to time, to summer 315. Summer 315 sums the first electrical signal $v_{235}(t)$ and the second differentiated electrical signal, and provides at node 510 a resulting combined electrical signal, $v_{510}(t)$, which is illustrated by Equation (7).

$$v_{510}(t)=V_{255}\sin(\omega t+\theta) \quad (7)$$

In Equation (7), the resulting combined electrical signal $v_{510}(t)$ has an amplitude, $V_{255}$, that is substantially independent of the angle $\theta$. However, the resulting combined electrical signal at node 510, $v_{510}(t)$, does have a phase dependence on the angle $\theta$, but this phase dependence can typically be accommodated by subsequent signal processing.

Figure 6:
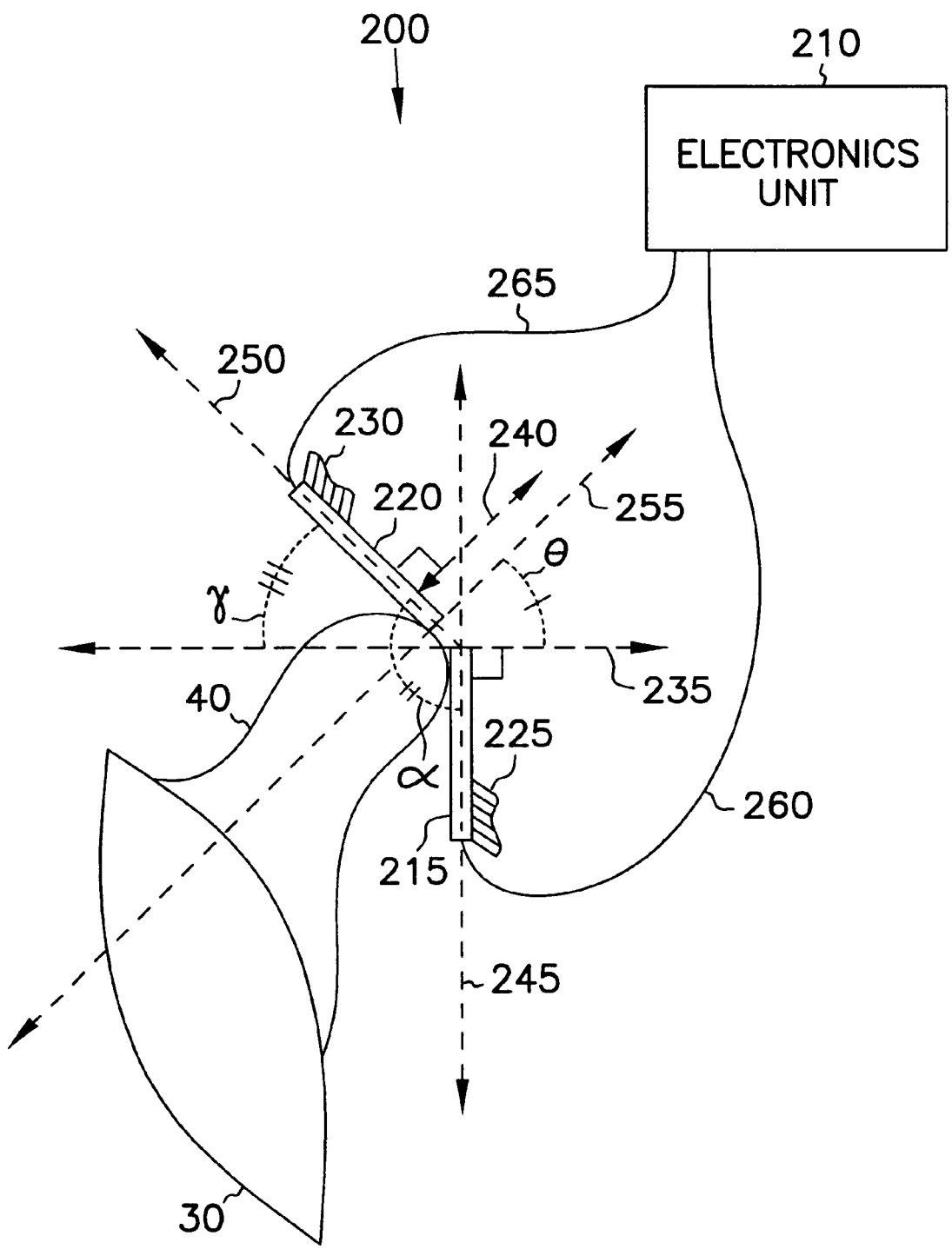
FIG. 6 is a schematic/block diagram illustrating generally another embodiment of the hearing assistance system of FIG. 2, in which the transducers are disposed in a more generalized arrangement.

FIG. 6 is a schematic/block diagram illustrating generally another embodiment of the hearing assistance system, including hearing assistance device 200, similar to the embodiment described with respect to FIG. 2. FIG. 2 illustrated one particular embodiment in which α is approximately equal to 90 degrees, i.e. having first transducer 215 and second transducer 220 that are disposed approximately orthogonal to each other. FIG. 6 illustrates a more generalized arrangement in which a is not approximately equal to 90 degrees, i.e. first transducer 215 and second transducer 220 are arranged in a predetermined spatial relationship, but need not be disposed approximately orthogonal to each other. Since first transducer 215 and second transducer 220 are arranged in a predetermined spatial relationship, a known angle γ is formed between the longitudinal direction 250 of second transducer 220 and the first directional component 235 of the vibration of malleus 40.

In FIG. 6, the resulting second electrical signal $v_{240}(t)$ is illustrated by Equation (8).

$$v_{240}(t) = V_{255} \cos(\gamma)\sin(\theta)\sin(\omega t) \tag{8}$$

The resulting second electrical signal $v_{240}(t)$ is scaled by a factor of $[1/\cos(\gamma)]$ by signal preprocessing components interposed between second lead 265 and one of the signal combiners described above with respect to FIGS. 3–5. The scaled second electrical signal is then combined with the first electrical signal $v_{235}(t)$ as described above with respect to FIGS. 3–5. As illustrated by FIG. 6, first transducer 215 and second transducer 220 need not be orthogonally disposed, but may be arranged in any predetermined spatial relationship.

Figure 7:
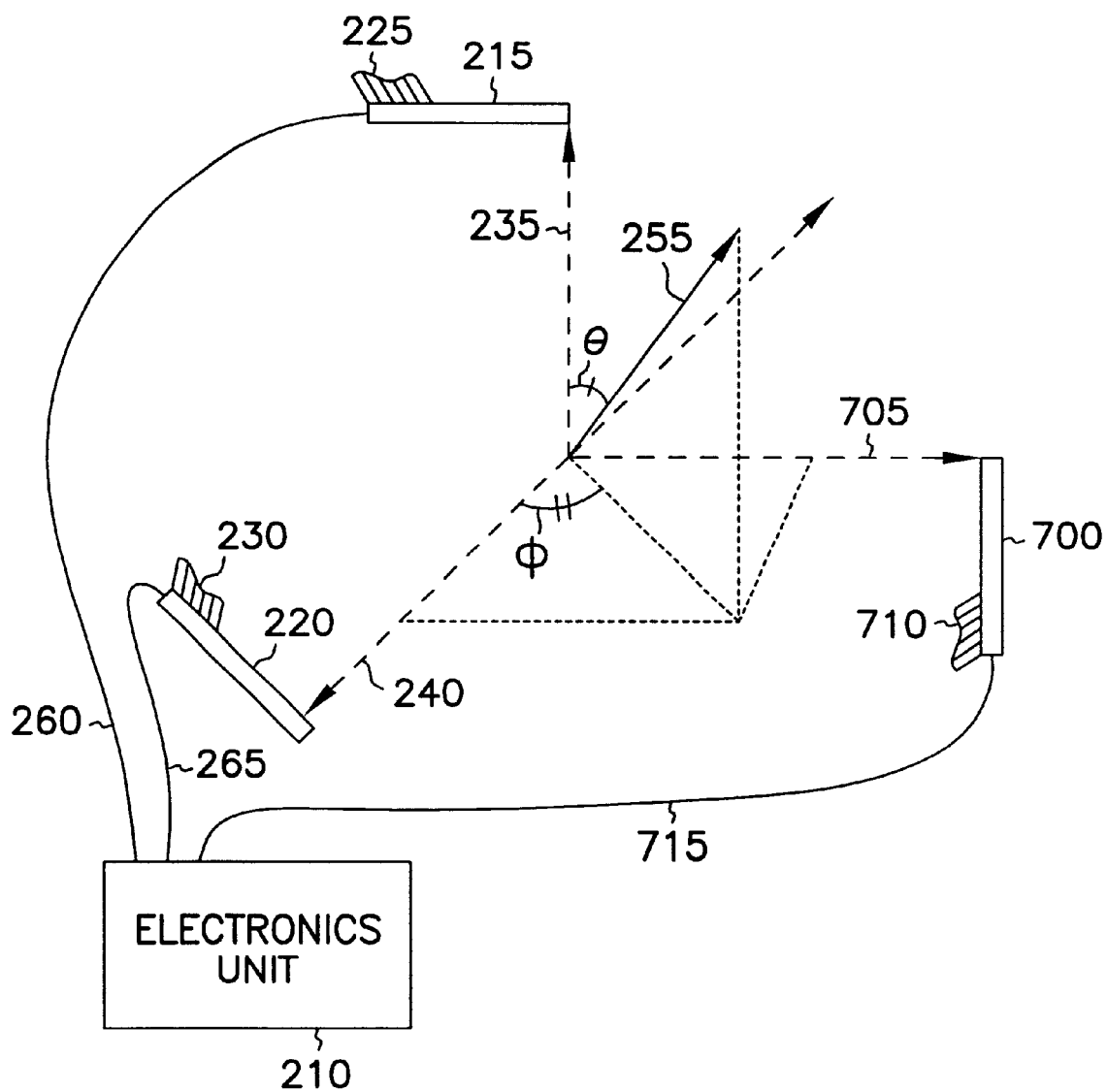
FIG. 7 is a schematic/block diagram illustrating generally another embodiment of a hearing assistance system, similar to that of FIG. 2, but including a third transducer.

FIG. 7 is a schematic/block diagram illustrating generally another embodiment of hearing assistance device 200, similar to the embodiment described with respect to FIG. 2, but including a third transducer 700. In FIG. 7, malleus 40 is omitted for clarity in order to better illustrate the vibration direction 255 along with one possible configuration of first, second, and third transducers 215, 220, and 700, respectively, having associated first, second, and third directional components 235, 240, and 705, respectively, that are nonidentical and linearly independent. Third transducer 700 is cantilevered from third mount 710 for transducing into a third electrical signal $v_{705}(t)$ the third directional component 705 of the vibratory motion of malleus 40. In this embodiment, the third directional component 705 is substantially orthogonal to the first and second directional components 235 and 240, respectively. An angle θ is formed between the vibration direction 255 and its first directional component 235. In FIG. 7, an angle φ is formed between vibration direction 255 and the plane formed by first directional component 235 and second directional component 240. A resulting first electrical signal, $v_{235}(t)$, is illustrated by Equation (9).

$$v_{235}(t) = V_{255} \cos(\theta)\sin(\omega t) \tag{9}$$

A resulting second electrical signal, $v_{240}(t)$, is illustrated by Equation (10).

$$v_{240}(t) = V_{255} \sin(\theta)\cos(\phi)\sin(\omega t) \tag{10}$$

A resulting third electrical signal, $v_{705}(t)$, is illustrated by Equation (11), and is coupled to electronics unit 210 through third lead 715.

$$v_{705}(t) = V_{255} \sin(\theta)\sin(\phi)\sin(\omega t) \tag{11}$$

Figure 7A:
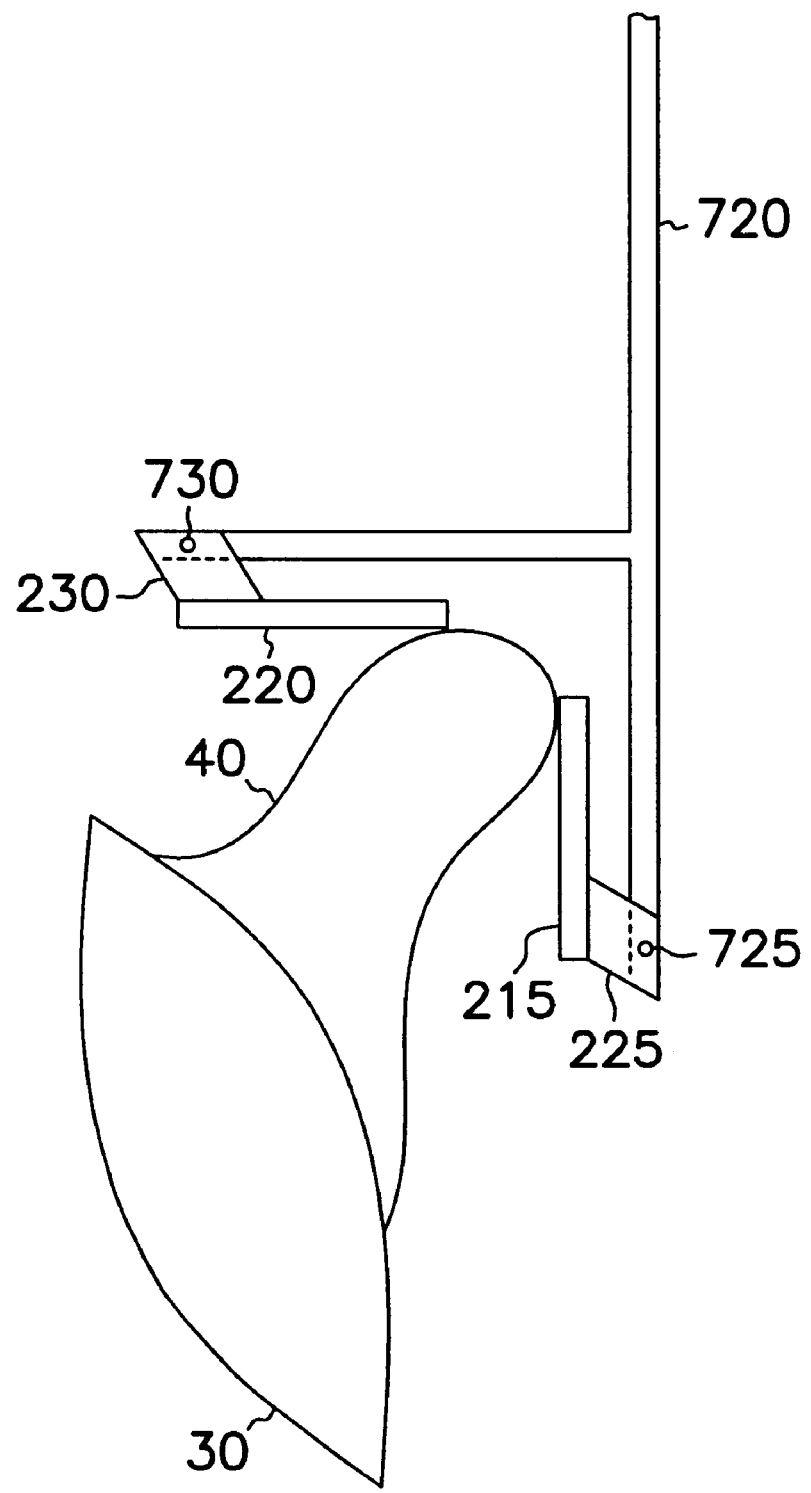
FIG. 7A is a schematic/block diagram illustrating one embodiment of a carrier to which input transducers are coupled.

In one embodiment, as illustrated in FIG. 7, first, second, and third transducers 215, 220, and 700 are disposed such that their associated first, second, and third directional components 235, 240, and 705 are approximately mutually orthogonal. However, it is understood that first, second, and third transducers 215, 220, and 700, respectively, need not be disposed such that their associated first, second, and third directional components 235, 240, and 705 are approximately mutually orthogonal. First, second, and third transducers 215, 220, and 700 need only be disposed in a predetermined spatial relationship such that their first, second, and third directional components 235, 240, and 705 are at known angles from an orthogonal basis; the resulting electrical signals can be individually scaled as described with respect to FIG. 6. For example, respective first, second, and third mounts 225, 230, and 710 may be integrally formed as a unitary carrier of respective first, second, and third transducers 215, 220, and 700, or mechanically coupled to such a carrier. Any carrier that provides a predetermined spatial arrangement of first, second, and third input transducers 215, 220, and 700 may be used. In one embodiment, the carrier provides an adjustably predetermined spatial arrangement of first, second, and third input transducers 215, 220, and 700. In another embodiment, carrier 720 provides an adjustable spatial arrangement of first and second input transducers 215 and 220, as illustrated in FIG. 7A, through respective first and second mounts 225 and 230 that are adjustably coupled to carrier 720, such as by set screws 725 and 730 respectively.

Figure 8:
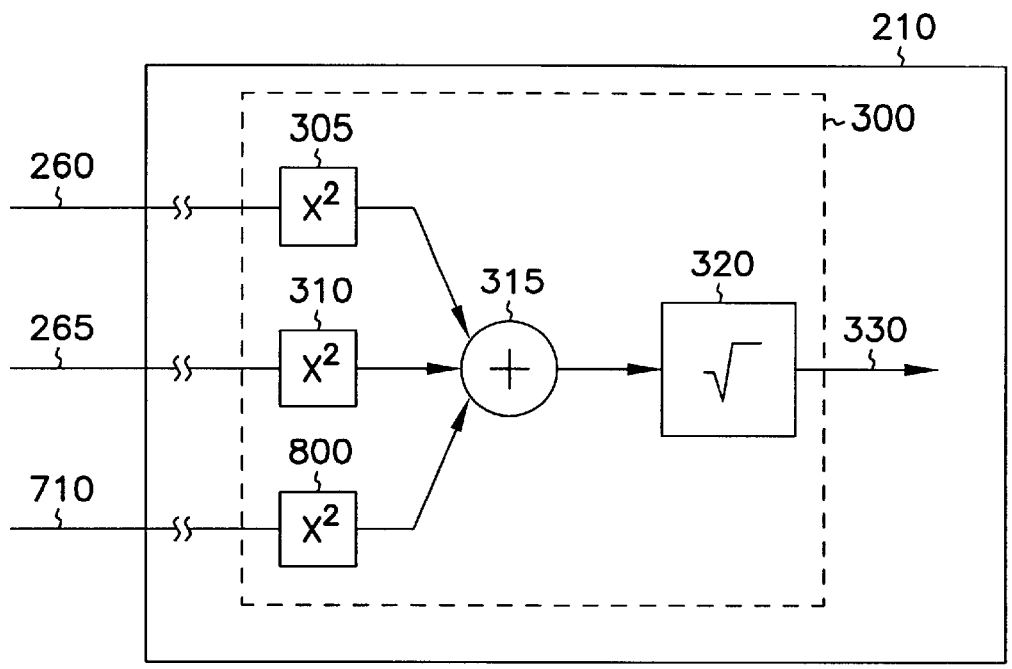
FIG. 8 is a block diagram, similar to FIG. 3, but including processing of a third electrical signal.

FIG. 8 is a block diagram, similar to FIG. 3, illustrating one embodiment of a signal combiner 300 that further includes a third squaring circuit 800 for squaring the third electrical signal, $v_{705}(t)$. In FIG. 8, the first electrical signal $v_{235}(t)$, the second electrical signal $v_{240}(t)$, and the third electrical signal $v_{705}(t)$ are each squared, i.e. raised to the power of two, the resulting squared signals are summed together by summer 315 to produce a sum-of-squares signal, and a square root function is then performed thereupon by square root circuit 320 to provide at node 330 a resulting combined electrical signal, described by Equation (6) that is independent of the angles θ and φ. As described above, since the angles θ and φ may be either unknown or variable, the substantial independence of the combined electrical signal at node 330 therefrom provides a substantial advantage for hearing assistance signal processing.

Figure 9:
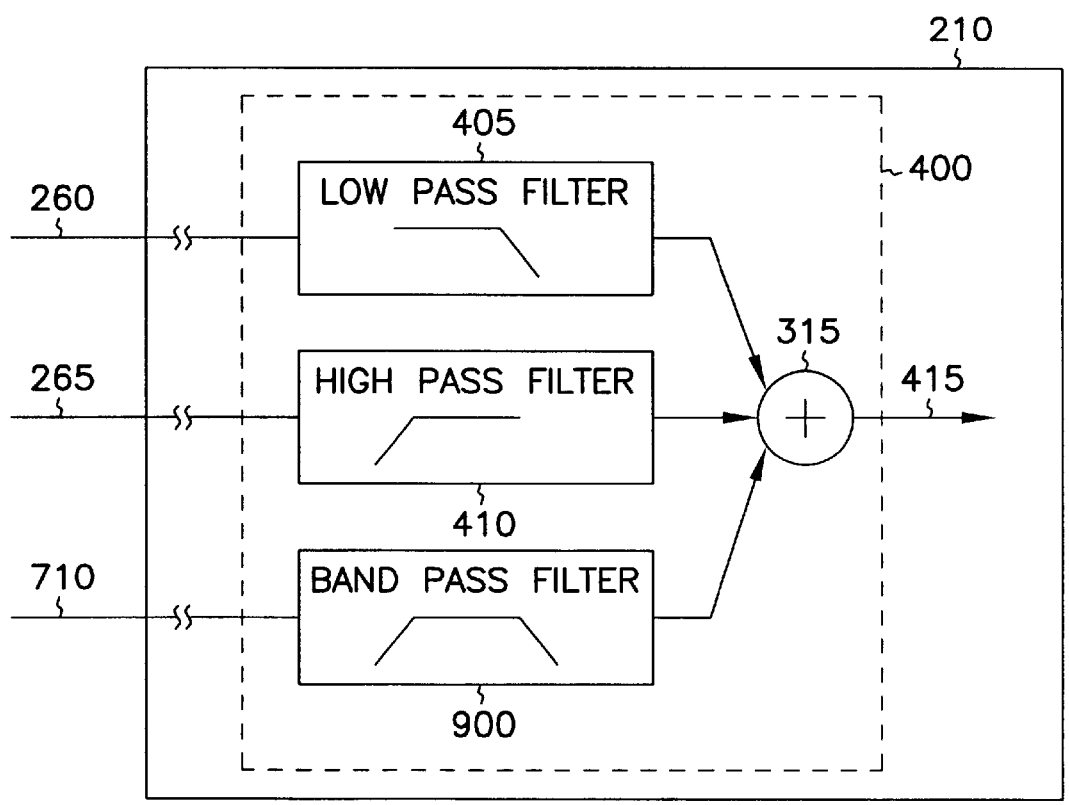
FIG. 9 is a block diagram, similar to FIG. 4, but including processing of a third electrical signal.

FIG. 9 is a block diagram, similar to FIG. 4, illustrating one embodiment of a signal combiner 400 that further includes a third filter 900, such as a bandpass filter for bandpass filtering the third electrical signal, $v_{705}(t)$. In FIG. 9, the first electrical signal $v_{235}(t)$, the second electrical signal $v_{240}(t)$, and the third electrical signal $v_{705}(t)$ are each filtered and summed together by summer 315 to provide at node 415 a resulting combined electrical signal, $v_{415}(t)$, which includes components of $v_{235}(t)$ for low frequencies, components of $v_{240}(t)$ for high frequencies, and components of $v_{705}(t)$ for intermediate frequencies. First transducer 215, second transducer 220, and third transducer 700 may be positioned to receive respective low, high, and intermediate frequency orientations of vibration direction 255.

Figure 10:
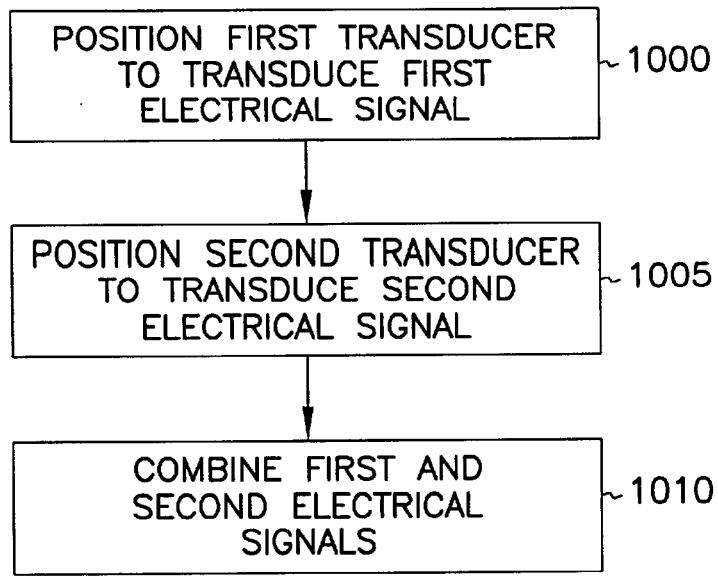
FIG. 10 is a flow chart summarizing one method of operating a hearing assistance device.

FIG. 10 is a flow chart summarizing one method of operating a hearing assistance device, such as hearing assistance device 200. At step 1000, a first input transducer 215 is positioned to transduce a first directional component 235 of the mechanical vibration of the auditory element into a first electrical signal $v_{235}(t)$. At step 1005, a second input transducer 220 is positioned to transduce a second directional component 240 of the mechanical vibration of the auditory element into a second electrical signal $v_{240}(t)$. At step 1010, the first electrical signal $v_{235}(t)$ is combined with the second electrical signal $v_{240}(t)$.

In one embodiment, the signal combination at step 1010 is by squaring, i.e. raising to the power of 2, each of the first electrical signal $v_{235}(t)$ and second electrical signal $v_{240}(t)$, summing the resulting squared signals, and taking the square root of the resulting sum-of-squares signal to provide a resulting combined electrical signal. One advantage of this embodiment is that the resulting combined electrical signal can be made independent of the vibration direction 255.

In another embodiment, the signal combination at step 1010 is by filtering the first electrical signal $v_{235}(t)$ by first filter 405, such as a low-pass filter, filtering the second electrical signal $v_{240}(t)$ by second filter 410, such as a high-pass filter, and summing the resulting filtered signals to provide a resulting combined electrical signal. One advantage of this embodiment is that it offers improved frequency response.

In yet another embodiment, the signal combination at step 1010 is by differentiating the second electrical signal $v_{240}(t)$, and summing the resulting second differentiated electrical signal with the first electrical signal $v_{235}(t)$ to provide a resulting combined electrical signal. One advantage of this embodiment is that the amplitude of the resulting combined electrical signal is independent of the vibration direction 255.

Figure 11:
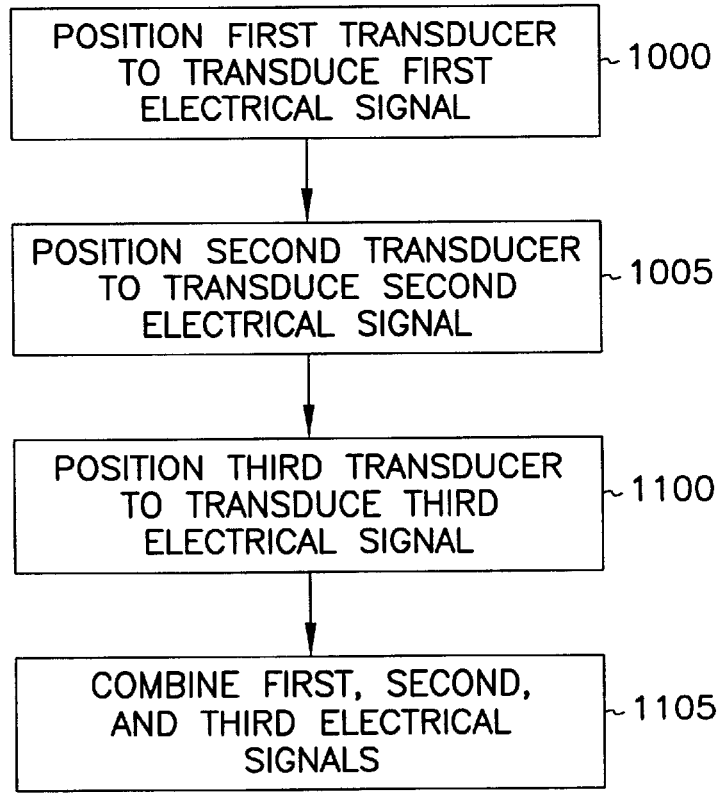
FIG. 11 is a flow chart summarizing another method of operating a hearing assistance device.

FIG. 11 is a flow chart summarizing another method of operating a hearing assistance device, such as hearing assistance device 200. At step 1000, a first input transducer 215 is positioned to transduce a first directional component 235 of the mechanical vibration of the auditory element into a first electrical signal $v_{235}(t)$. At step 1005, a second input transducer 220 is positioned to transduce a second directional component 240 of the mechanical vibration of the auditory element into a second electrical signal $v_{240}(t)$. At step 1100, a third input transducer 700 is positioned to transduce a third directional component 705 of the mechanical vibration of the auditory element into a third electrical signal $v_{705}(t)$. At step 1105, the first electrical signal $v_{235}(t)$, second electrical signal $v_{240}(t)$, and third electrical signal $v_{705}(t)$ are combined to provide a resulting combined electrical signal.

In one embodiment, the signal combination of step 1105 is by squaring, i.e. raising to the power of 2, each of the first electrical signal $v_{235}(t)$, second electrical signal $v_{240}(t)$, and third electrical signal $v_{705}(t)$, summing the resulting squared signals, and taking the square root of the resulting sum-of-squares signal to provide a resulting combined electrical signal. One advantage of this embodiment is that the resulting combined electrical signal can be made independent of the vibration direction 255.

In another embodiment, the signal combination of step 1105 is by filtering the first electrical signal $v_{235}(t)$ by first filter 405, such as a low-pass filter, filtering the second electrical signal $v_{240}(t)$ by second filter 410, such as a high-pass filter, filtering the third electrical signal $v_{705}(t)$ by third filter 900, such as a band-pass filter, and summing the resulting filtered signals to provide a resulting combined electrical signal. One advantage of this embodiment is that it offers improved frequency response. In one embodiment, the above-described signal combination techniques are programmably selected using programmer 201.

Thus, the present invention includes an improved hearing assistance system for sensing sound vibrations in the middle ear. The hearing assistance system accommodates variability in the direction of motion of an ossicular or other auditory element. This is particularly advantageous for sensing mechanical vibrations of an auditory element where the exact direction of the mechanical vibrations may be unknown, variable, or difficult to determine.

It is to be understood that the above description is intended to be illustrative, and not restrictive. Combinations of the above-described illustrative embodiments are also included within the present invention. Many other embodiments will be apparent to those of skill in the art upon reviewing the above description. The scope of the invention should, therefore, be determined with reference to the appended claims, along with the full scope of equivalents to which such claims are entitled.

What is claimed is:

1. A method of transducing a mechanical vibration of an auditory element into at least one electrical signal, the method comprising the steps of:

positioning a first input transducer to transduce a first directional component of the mechanical vibration into a first electrical signal;

positioning a second input transducer to transduce a second directional component of the mechanical vibration into a second electrical signal, wherein the first and second directional components of the mechanical vibration are nonidentical; and combining the first and second electrical signals to provide a resulting combined electrical signal including:
squaring each of the first and second electrical signals to provide resulting first and second squared electrical signals;
summing each of the first and second squared electrical signals to provide a resulting sum-of-squares signal; and
taking the square root of the sum-of-squares signal to provide a resulting combined electrical signal.

2. An at least partially implantable hearing assistance system, comprising:

a sensor for transducing a mechanical vibration of an auditory element into an electrical signal, the sensor including:
a first input transducer, proportioned for transducing a first directional component of the mechanical vibration into a first electrical signal; and
a second input transducer, proportioned for transducing a second directional component of the mechanical vibration into a second electrical signal, wherein the first and second directional components of the mechanical vibration are nonidentical; and an electronics unit, coupled to the sensor for receiving the first and second electrical signals therefrom, including:
a first squaring circuit, receiving the first electrical signal and providing a first squared electrical signal in response thereto;
a second squaring circuit, receiving the second electrical signal and providing a second squared electrical signal in response thereto;
a summer, receiving each of the first and second squared electrical signals and providing a resulting sum-of-squares electrical signal in response thereto; and
a square root circuit, receiving the sum-of-squares electrical signal and providing a combined electrical signal in response thereto.

3. A method of transducing a mechanical vibration of an auditory element into at least one electrical signal, the method comprising the steps of:

positioning a first input transducer to transduce a first directional component of the mechanical vibration into a first electrical signal;

positioning a second input transducer having frequency characteristics substantially identical to the first input transducer to transduce a second directional component of the mechanical vibration into a second electrical signal, wherein the first and second directional components of the mechanical vibration are nonidentical and the positioning of the transducers is in a predetermined spatial arrangement; and combining the first and second electrical signals to provide a resulting combined electrical signal including the steps of:

squaring each of the first and second electrical signals to provide resulting first and second squared electrical signals;

summing each of the first and second squared electrical signals to provide a resulting sum-of-squares signal; and taking the square root of the sum-of-squares signal to provide a resulting combined electrical signal.

4. An at least partially implantable hearing assistance system, comprising:

a) a sensor for transducing a mechanical vibration of an auditory element into an electrical signal, the sensor including:

a first input transducer, proportioned for transducing a first directional component of the mechanical vibration into a first electrical signal; and a second input transducer having frequency characteristics substantially identical to the first input transducer, proportioned for transducing a second directional component of the mechanical vibration into a second electrical signal, wherein the first and second directional components of the mechanical vibration are nonidentical and the first and second input transducers are physically located so that the sensing structure of the input transducers is in a predetermined angular relation to optimize the signal processing; and b) an electronics unit, coupled to the sensor for receiving the first and second electrical signals therefrom, including:

a first squaring circuit, receiving the first electrical signal and providing a first squared electrical signal in response thereto;

a second squaring circuit, receiving the second electrical signal and providing a second squared electrical signal in response thereto;

a summer, receiving each of the first and second squared electrical signals and providing a resulting sum-of-squares electrical signal in response thereto; and a square root circuit, receiving the sum-of-squares electrical signal and providing a combined electrical signal in response thereto.

* * * * *